United States Patent

Griffith

[11] Patent Number: 4,569,994
[45] Date of Patent: Feb. 11, 1986

[54] DIBENZO[B,D]PYRANYLOXYAMINO-PROPANOLS

[75] Inventor: Ronald C. Griffith, Pittsford, N.Y.

[73] Assignee: Pennwalt Corporation, Philadelphia, Pennsylvania

[21] Appl. No.: 749,321

[22] Filed: Jun. 27, 1985

Related U.S. Application Data

[63] Continuation-in-part of Ser. No. 533,475, Sep. 19, 1983.

[51] Int. Cl.[4] .................. C07D 311/80; C07D 413/12
[52] U.S. Cl. ........................ 544/150; 544/58.7; 544/375; 546/196; 548/262; 548/336; 548/374; 548/525; 549/280; 549/390; 260/330.9
[58] Field of Search .............. 544/58.7, 150, 375; 546/196; 548/262, 374, 336, 525; 260/330.9; 549/280, 390

[56] References Cited

U.S. PATENT DOCUMENTS 3,649,650  3/1972  Razdan et al. ............... 549/390

Primary Examiner—Robert W. Ramsuer

[57] ABSTRACT

Dibenzopyran derivatives which possess antihypoxia activity are 7,8,9,10-tetrahydro-6H-dibenzo[b,d]pyranyloxyaminopropanols having the formula:

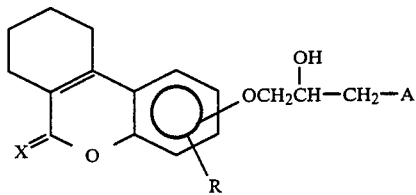

Where X is oxygen or dialkyl in which each alkyl group contains one to seven carbons ($C_1$–$C_7$); R is hydrogen or alkyl containing one to seven carbons ($C_1$–$C_7$); and A is —$NR_1R_2$ where $R_1$ and $R_2$ may independently be hydrogen, $C_1$–$C_7$ alkyl, $C_3$–$C_7$ cycloalkyl, phenyl, $C_7$–$C_{10}$ phenylalkyl, $C_7$–$C_{10}$ phenoxyalkyl, $C_2$–$C_6$ alkanol, 6-oxo-6H-dibenzo[b,d]pyran-3-yl, 2-hydroxy-3-(7,8,9,10-tetrahydro-6-oxo-6H-dibenzo[b,d]pyranyl-3-oxy)-propyl; or A is a heterocyclic ring of structure:

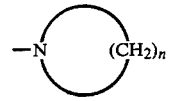

where n=2 or 3; or A is a substituted heterocyclic ring of structure:

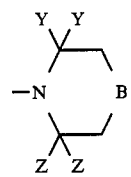

where Y and Z may be independently hydrogen or methyl and B represents a single bond, methylene, ethylene, propylene, CH-phenyl, $CHCH_2$-phenyl, oxygen, sulfur, or N—$R_4$ where $R_4$ is hydrogen, $C_1C_4$ alkyl, formyl, phenyl, or benzyl and where the phenyl rings may additionally be substituted with halogen, methoxy, methyl, $CF_3$, or various combinations thereof; or where A is an unsaturated heterocyclic ring taken to be 1-imidazolyl, 1-pyrrolyl, 1-pyrazolyl or 1-[1,2,4-triazolyl].

12 Claims, No Drawings

DIBENZO[B,D]PYRANYLOXYAMINO-PROPANOLS

This application is a continuation-in-part of application Ser. No. 533,475 filed Sept. 19, 1983.

BACKGROUND OF THE INVENTION

This invention relates generally to dibenzopyran derivatives and more specifically to certain 7,8,9,10-tetrahydro-6H-dibenzo[b,d]pyranyloxyaminopropanols.

The compounds of this invention possess useful antihypoxia activity, that is they protect warm-blooded animals from the effects of oxygen deprivation.

BRIEF SUMMARY OF THE INVENTION

In accordance with this invention, there are provided 7,8,9,10-tetrahydro-6H-dibenzo[b,d]pyranyloxyaminopropanols having the following structural formula (1):

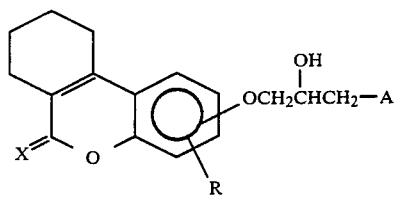

where X is oxygen or dialkyl in which each alkyl group contains one to seven carbons ($C_1$–$C_7$); R is hydrogen or alkyl containing one to seven carbons ($C_1$–$C_7$); and A is —$NR_1R_2$ where $R_1$ and $R_2$ may independently be hydrogen, $C_1$–$C_7$ alkyl, $C_3$–$C_7$ cycloalkyl, phenyl, $C_7$–$C_{10}$ phenylalkyl, $C_7$–$C_{10}$ phenoxyalkyl, $C_2$–$C_6$ alkanol, 6-oxo-6H-dibenzo[b,d]pyran-3-yl, 2-hydroxy-3-(7,8,9,10-tetrahydro-6-oxo-6H-dibenzo[b,d]pyranyl-3-oxy)propyl; or A is a heterocyclic ring of structure:

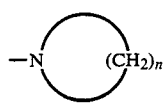

where n=2 or 3; or A is a substituted heterocyclic ring of structure:

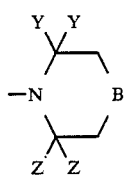

where Y and Z may be independently hydrogen or methyl and B represents a single bond, methylene, ethylene, propylene, CH-phenyl, $CHCH_2$-phenyl, oxygen, sulfur, or N—$R_4$ where $R_4$ is hydrogen, $C_1$–$C_4$ alkyl, formyl, phenyl, or benzyl and where the phenyl rings may additionally be substituted with halogen, methoxy, methyl, $CF_3$, or various combinations thereof; or where A is an unsaturated heterocyclic ring taken to be 1-imidazolyl, 1-pyrrolyl, 1-pyrazolyl or 1-[1,2,4-triazolyl].

This invention also includes acid addition salts of these compounds and the method of preparing the compounds.

DETAILED DESCRIPTION

The compounds of the invention can be conveniently prepared from 3-hydroxy and 1-hydroxy-3-methyl-7,8,9,10-tetrahydro-6H-dibenzo[b,d,]pyrone and -pyrans which are known compounds. The pyrone and pyran starting materials can be prepared as described in R. Adams and B. R. Baker, *J. Am. Chem. Soc.*, 62, 2405 (1940). Thus, condensing orcinol or resorcinol with ethyl cyclohexanone-2-carboxylate in the presence of phosphorus oxychloride, gives the corresponding pyrones (formula 2 where X is oxygen), which are converted to the 6,6-dialkyl pyrans (formula 2 where X is dialkyl) upon treatment with an alkyl magnesium iodide such as methyl magnesium iodide.

Treatment of these phenolic pyrans (2) with an alkali hydroxide such as sodium or potassium hyroxide, and an excess of an epihalohydrin, such as epichlorohydrin in a suitable inert solvent, gives the corresponding epoxides (3), where X and R are as described for (1).

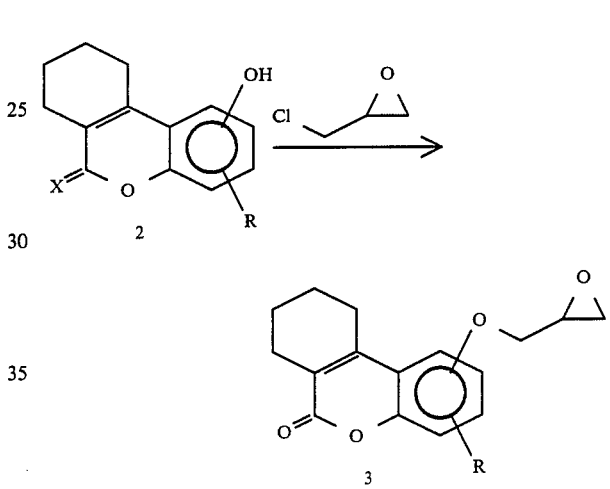

The compounds of general formula 1, where A is primary secondary or tertiary amino, are prepared from the epoxides (formula 3) by treatment with a solution of ammonia or the corresponding primary or secondary amine in a suitable Solvent (e.g. methanol, chloroform, tetrahydrofuran).

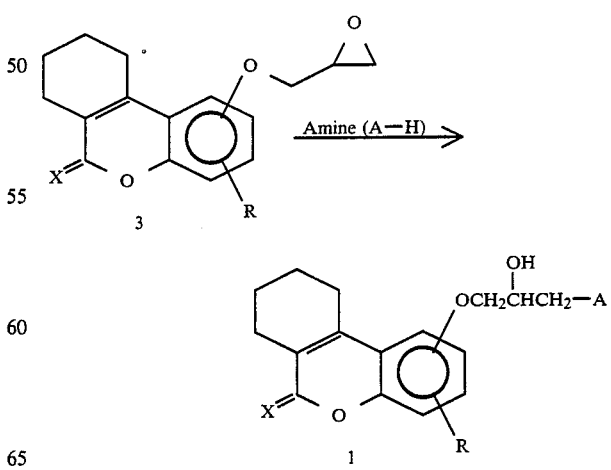

The compounds of the invention also include quarternary ammonium and acid addition salts which are pharmaceutically acceptable. Acid addition salts include those derived from both organic and inorganic acids such as, for example, acetic acid, maleic acid, malic acid, fumaric acid, succinic acid, succinamic acid, tartaric acid, citric acid, lactic acid, hydrochloric acid, hydrobromic acid, hydriodic acid, sulfuric acid, phosphoric acid, and the like.

Amines which can be reacted to form the compounds of the invention include A-H where

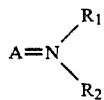

and where $R_1$ and $R_2$ may independently be hydrogen, $C_1$-$C_7$ alkyl, $C_3$-$C_7$ cycloalkyl, phenyl, $C_7$-$C_{10}$ phenylalkyl, $C_7$-$C_{10}$ phenoxyalkyl, $C_2$-$C_6$ alkanol, or where $R_1$ and $R_2$ taken together comprise a heterocyclic ring containing 1–4 heteroatoms and 2–7 carbon atoms.

The following specific examples are provided to illustrate the preparation of the epoxides (3) and their conversion to the compounds of general formula (1) by treatment with a variety of amines.

PREPARATION OF INTERMEDIATES

Procedure 1

Preparation of 7,8,9,10-tetrahydro-3-methyl-1-(oxiranylmethoxy)-6-oxo-6H-dibenzo[b,d]pyran To a stirred solution of NaOH (4.0 g, 0.1 m) in dimethylsulfoxide (DMSO) (250 ml) and water (250 ml), was added 7,8,9,10-tetrahydro-1-hydroxy-3-methyl-6-oxo-6H-dibenzo[b,d]pyran (20.0 g, 0.087 m) and the mixture stirred for 5 minutes, then treated with epichlorohydrin (50 ml). After 5 hours the mixture was cooled in an ice bath for 30 minutes and the precipitated solid collected by filtration, washed with water and dried to give 7,8,9,10-tetrahydro-3-methyl-1-(oxiranylmethoxy)-6-oxo-6H-dibenzo[b,d]pyran as a white solid, mp. 164°–165° C. An analytical sample recrystallized from methanol melted at 165°–166° C.

Procedure 2

Preparation of 7,8,9,10-tetrahydro-3-(oxiranylmethoxy)-6-oxo-6H-dibenzo[b,d]pyran To a stirred solution of NaOH (2.0 g, 0.05 m) in DMSO (125 ml) and water (125 ml) was added 7,8,9,10-tetrahydro-3-hydroxy-6-oxo-6H-dibenzo[b,d]pyran (10.0 g, 0.046 m). When a solution was obtained, the mixture was treated with epichlorohydrin (35 ml) and stirred for 56 hours. A white solid precipitated which was collected by filtration to give 12.1 g of a mixture consisting of ca. 90% 7,8,9,10-tetrahydro-3-(oxiranylmethoxy)-6-oxo-6H-dibenzo[b,d]pyran. The pure epoxide was obtained by chromatography on $SiO_2$ and crystallization from methanol/chloroform to give 8.0 g of white solid, mp. 120°–121° C.

Procedure 3

Preparation of 7,8,9,10-tetrahydro-3,6,6-trimethyl-1(oxiranylmethoxy)-6H-dibenzo[b,d]pyran To a stirred solution of NaOH (2.4 g, 0.06 m) in DMSO (125 ml) and water (125 ml) was added 7,8,9,10-tetrahydro-3,6,6-trimethyl-1-hydroxy-6H-dibenzo[b,d]pyran (13.1 g, 0.054 m) in DMSO (125 ml) and water (125 ml) and then epichlorohydrin (34.8 g, 0.376 m) and the mixture stirred for 5 hours, treated with water (0.5 L) and extracted with ether (3×300 ml). The combined ether extracts were dried over $MgSO_4$ and evaporated to give 7,8,9,10-tetrahydro-3,6,6-trimethyl-1-(oxiranylmethoxy)-6H-dibenzo[b,d]pyran as a pale yellow oil, 14.0 g. This material was of sufficient purity to use as is for further chemical processing.

Procedure 4

Preparation of 7,8,9,10-tetrahydro-6,6-dimethyl-3-(oxiranylmethoxy)-6H-dibenzo[b,d]pyran To a stirred solution of NaOH (4.0 g, 0.1 m) DMSO (250 ml) and water (250 ml) was added 7,8,9,10-tetrahydro-6,6-dimethyl-3-hydroxy-6H-dibenzo[b,d]pyran (21.3 g, 0.0926 m) and then epichlorohydrin (60 g, 0.648 m) and the mixture stirred for 5 hours, treated with water (1 L) and extracted with ether (3×500 ml). The combined extracts were dried over $MgSO_4$ and evaporated to give 7,8,9,10-tetrahydro-6,6-dimethyl-3-(oxiranylmethoxy)-6H-dibenzo[b,d]pyran as a pale yellow oil, 23.2 g. This material was of sufficient purity to use as is for further chemical processing.

EXAMPLE 1

Preparation of 3-(7,8,9,10-tetrahydro-6-oxo-6H-dibenzo[b,d]pyranyl-3-oxy)-1-(1-methylethyl)amino-2-propanol hydrochloride To a stirred solution of 7,8,9,10-tetrahydro-3-(oxiranylmethoxy)-6-oxo-6H-dibenzo[b,d]pyran (11.6 g, 0.0426 m) in methanol (250 ml) was added isopropyl amine (25 ml) and the mixture heated to reflux for 1 hour, cooled, and the solvent evaporated. The residue was dissolved in chloroform (200 ml) and 5% HCl (250 ml), the layers separated and the aqueous phase extracted with (2×100 ml) chloroform. The combined chloroform extracts were backwashed with 100 ml 5% HCl and the combined aqueous acid layers were basified to pH 11 with NaOH, and extracted with chloroform (3×200 ml). These extracts were dried and evaporated to a white solid 11.8 g. This was dissolved in methanol/isopropanol, acidified with HCl gas and the salt allowed to crystallize. The white solid was collected by filtration, recrystallized a second time and vacuum dried to give 9.5 g of 3-(7,8,9,10-tetrahydro-6-oxo-6H-dibenzo[b,d]pyranyl-3-oxy)-1-(1-methylethyl)amino-2-propanol hydrochloride, mp. 205°–206° C.

EXAMPLE 2

Preparation of 3-(7,8,9,10-tetrahydro-3-methyl-6-oxo-6H-dibenzo[b,d]pyranyl-1-oxy)-1-(1-methylethyl)amino-2-propanol hydrochloride A solution of 7,8,9,10-tetrahydro-3-methyl-1-(oxiranylmethoxy)-6-oxo-6H-dibenzo[b,d]pyran (12 g, 0.042 m) in methanol (250 ml) was treated with isopropylamine (25 ml) and the mixture stirred and heated to reflux for 1 hour, cooled, and the solvent evaporated to an oil that solidified on standing. This was dissolved in methanol (50 ml) and isopropanol (50 ml), acidified with HCl gas and the salt allowed to crystallize. The white solid was collected by filtration and vacuum dried to give 8.4 g of 3-(7,8,9,10-tetrahydro-3-methyl-6- oxo-6H-dibenzo[b,d]pyranyl-1-oxy)-1-(1-methylethyl)amino-2-propanol hydrochloride, mp. 259°–260° C.

EXAMPLE 3

Preparation of
3-(7,8,9,10-tetrahydro-3-methyl-6-oxo-6H-dibenzo[b,d]pyranyl-1-oxy)-1-(1,1-dimethylethyl)amino-2-propanol hydrochloride A solution of 7,8,9,10-tetrahydro-3-methyl-1-(oxiranylmethoxy)-6-oxo-6H-dibenzo[b,d]pyran (9.4 g, 0.033 m) in methanol (250 ml) was treated with t-butylamine and the mixture stirred and heated to reflux for 1 hour, cooled, and the solvent evaporated to an off-white solid. This material was purified by chromatography on a Prep 500 HPLC, on silica gel, eluting with chloroform and ammoniated methanol to give a white solid, 11.5 g. This was dissolved in methanol (150 ml) and isopropanol and acidified with HCl gas. Upon standing a white solid crystallized which was collected by filtration and vacuum dried to give 12.0 g of 3-87,8,9,10-tetrahydro-3-methyl-6-oxo-6H-dibenzo[b,d]pyranyl-1-oxy-1-(1,1-dimethylethyl)amino-2-propanol hydrochloride, mp. 304°–305° C.

EXAMPLE 4

Preparation of
3-(7,8,9,10-tetrahydro-3-methyl-6-oxo-6H-dibenzo[b,d]pyranyl-1-oxy)-1-(1-methyl-2-phenoxyethyl)amino-2-propanol hydrochloride To a stirred solution of 7,8,9,10-tetrahydro-3-methyl-1-(oxiranylmethoxy)-6-oxo-6H-dibenzo[b,d]pyran (11.8 g, 0.041 m) in methanol (250 ml) was added 1-methyl-2-phenoxyethylamine (15 g, 0.1 m) and the mixture refluxed for 5 hours, cooled, and the solvent evaporated. The residue was dissolved in chloroform (2×50 ml) and the combined chloroform extracts dried and evaporated to a foamy solid residue. This was recrystallized twice from a mixture of ethanol, chloroform, and ether and vacuum dried to give 9.1 g of 3-(7,8,9,10-tetrahydro-3-methyl-6-oxo-6H-dibenzo[b,d]pyranyl-1-oxy)-1-(1-methyl-2-phenoxy ethyl)amino-1-propanol hydrochloride as a white solid, mp. 202°–203° C.

EXAMPLE 5

Preparation of
3-(7,8,9,10-tetrahydro-6,6-dimethyl-6H-dibenzo[b,d]pyranyl-3-oxy)-1-(1-methylethyl)amino-2-propanol hydrochloride To a stirred solution of 7,8,9,10-tetrahydro-6,6-dimethyl-3-(oxiranylmethoxy)-6H-dibenzo[b,d]pyran in methanol (500 ml) was added isopropylamine (50 ml) and the mixture heated to reflux for 1 hour, cooled and the solvent evaporated to a solid residue. This was dissolved in isopropanol (50 ml) and ether (350 ml) and acidified with HCl gas. On cooling, a white solid crystallized, which was recrystallized twice and vacuum dried to give 9.1 g of 3-(7,8,9,10-tetrahydro-6,6-dimethyl-6H-dibenzo[b,d]pyranyl-3-oxy)-1-(1-methylethyl)amino-2-propanol hydrochloride, mp 184°–186° C.

EXAMPLE 6

Preparation of
3-(7,8,9,10-tetrahydro-3,6,6-trimethyl-6H-dibenzo[b,d]pyranyl-1-oxy)-1-(1-methylethyl)amino-2-propanol hydrochloride To a stirred solution of 7,8,9,10-tetrahydro-3,6,6-trimethyl-1-(oxiranylmethoxy)-6H-dibenzo[b,d]pyran (14 g, 0.046 m) in methanol (250 ml) was added isopropylamine (30 ml) and the mixture heated to reflux for 1 hour, cooled, and the solvent evaporated. The residue was purified by chromatography on a Prep 500 HPLC, on silica gel, eluting with chloroform and ammoniated methanol, to give a yellow oil. This was dissolved in isopropanol (200 ml) and ether (300 ml), acidified with HCl gas. Upon standing, a white solid crystallized which was collected by filtration and vacuum dried to give 8.7 g of 3-(7,8,9,10-tetrahydro-3,6,6-trimethyl-6H-dibenzo[b,d]pyranyl-1-oxy)-1-(1-methylethyl)amino-2-propanol hydrochloride, mp 180°–182° C.

EXAMPLE 7

Preparation of
3-(7,8,9,10-tetrahydro-3,6,6-trimethyl-6H-dibenzo[b,d]pyranyl-1-oxy)-1-(1,1-dimethylethyl)amino-2-propanol hydrochloride To a stirred solution of 7,8,9,10-tetrahydro-3,6,6-trimethyl-1-(oxiranylmethoxy)-6H-dibenzo[b,d]pyran (18 g, 0.06 m) in methanol (250 ml) was added t-butylamine (30 ml) and the mixture heated to reflux for 1 hour, cooled, and the solvent evaporated to an oil. The oil was dissolved in isopropanol (100 ml) and ether (300 ml), hot filtered, and acidified with HCl gas. Upon addition of ether (100 ml) and cooling, a solid crystallized which was collected by filtration, recrystallized as above and dried under vacuum to give 6.0 g of 3-(7,8,9,10-tetrahydro-3,6,6-trimethyl-6H-dibenzo[b,d]pyranyl-1-oxy)-1-(1,1-dimethylethyl)amino-2-propanol hydrochloride as a white solid, mp. 158°–160° C.

EXAMPLE 8

Preparation of
3-(7,8,9,10-tetrahydro-3,6,6-trimethyl-6H-dibenzo[b,d]pyranyl-1-oxy)-1-methylamino-2-propanol hydrochloride To a stirred solution of 7,8,9,10-tetrahydro-3,6,6-trimethyl-1-(oxiranylmethoxy)-6H-dibenzo[b,d]pyran (12.4 g, 0.041 m) in methanol (500 ml) was added methylamine (50 ml) and the mixture stirred to 25° C. for 4 hours, then 50° C. for 1 hour. The mixture was allowed to cool and the solvent evaporated to an oil, 14.2 g. This was purified by chromatography on a Prep 500 HPLC on silica gel, eluting with ammoniated methanol and chloroform to give an oil, 9.8 g. This was dissolved in isopropanol (50 ml) and ether (200 ml) and acidified with HCl gas. Upon standing, a white solid crystallized, which was collected, recrystallized and vacuum dried to give 5.4 g of 3-(7,8,9,10-tetrahydro-3,6,6-trimethyl-6H-dibenzo[b,d]pyranyl-1-oxy)-1-methylamino-2-propanol hydrochloride, mp. 187°–188° C.

EXAMPLE 9

Preparation of
3-(7,8,9,10-tetrahydro-6-oxo-6H-dibenzo[b,d]pyranyl-3-oxy)-1-(1-piperidinyl)-2-propanol hydrochloride To a stirred solution of 7,8,9,10-tetrahydro-3-(oxiranylmethoxy)-6-oxo-6H-dibenzo[b,d]pyran (10.0 g, 0.036 m) is methanol (250 ml) and chloroform (50 ml) under an atmosphere of nitrogen was added piperidine (3.46 g, 0.04 m) and the mixture stirred 18 hours. The solvent was evaporated to a residue, 13.4 g, which was purified by chromatography on a Prep 500 HPLC, on silica gel, eluting with chloroform and 5% ammoniated methanol to give an oil. This was dissolved in isopropanol (100 ml) and methanol (100 ml) and acidified with HCl gas. Upon standing, a white solid crystallized which was collected by filtration and vacuum dried to give 4.0 g of 3-(7,8,9,10-tetrahydro-6-oxo-6H-dibenzo[b,d]pyranyl-3-oxy)-1-(1-piperidinyl)-2-propanol hydrochloride, mp. 226°–227° C.

Following the procedure essentially as outlined above and substituting hexamethyleneimine, ethyleneimine, trimethyleneimine, 4-phenylpiperidine, 2,2,6,6-tetramethylpiperidine, 4-benzylpiperidine, piperazine, N-formylpiperazine, N-methylpiperazine, N-phenylpiperazine, N-benzylpiperazine, N-(4-fluorophenyl)piperazine, N-(3-chlorophenyl)piperazine, N-[3-(trifluoromethyl)phenyl]piperazine, N-(4-methoxyphenyl)piperazine, N-(2-methylphenyl)piperazine for piperidine will result in the preparation of the corresponding 3-(7,8,9,10-tetrahydro-6-oxo-6H-dibenzo[b,d]pyranyl-3-oxy)-1-(1-hexamethyleneiminyl), mp. 205°–206° C.; 1-(1-ethyleneiminyl); 1-(1-trimethyleneiminyl) 1-[1-(4-phenylpiperidinyl)], mp. 263°–264° C.; 1-[1-(2,2,6,6-tetramethylpiperidinyl)], mp. 261°–262° C.; 1-[1-(4-benzylpiperidinyl)]; 1-(1-piperazinyl); 1-[1-(4-formylpiperazinyl)]; 1-[1-(4-methylpiperazinyl)]; 1-[1-(4-phenylpiperazinyl)]; 1-[1-(4-benzylpiperazinyl)], mp. 269°–271° C.; 1-[1-[4-(4-fluorophenyl)piperazinyl]], mp. 235°–236° C.; 1-[1-[4-(3-chlorophenyl)-piperazinyl]], mp. 238°–239° C.; 1-[1-[4-(3-trifluorophenyl)piperazinyl]]; 1-[1-[4-(4-methoxyphenyl)piperazinyl]]; and 1-[1-[4-(2-methylphenyl)piperazinyl]]-2-propanols respectively.

EXAMPLE 10

Preparation of 3-(7,8,9,10-tetrahydro-6-oxo-6H-dibenzo[b,d]pyranyl-3-oxy)-1-ethylamino-2-propanol hydrochloride To a stirred solution of 7,8,9,10-tetrahydro-3-(oxiranylmethoxy)-6-oxo-6H-dibenzo[b,d]pyran (10.0 g, 0.036 m) in methanol (250 ml) and chloroform (50 ml) under an atmosphere of nitrogen was added monoethylamine (25 mls) and the mixture stirred 48 hours. The solvent was evaporated to a residue, 13.4 g, which was purified by chromatography on a Prep 500 HPLC, on silica gel, eluting with chloroform and 5% ammoniated methanol to give a solid residue. This was dissolved in absolute ethanol (150 ml) and acidified with HCl gas. Upon standing, a white solid crystallized which was collected by filtration and vacuum dried to give 10.6 g of 3-(7,8,9,10-tetrahydro-6-oxo-6H-dibenzo[b,d]pyranyl-3-oxy)-1-ethylamino-2-propanol hydrochloride, mp. 193°–194° C.

EXAMPLE 11

Preparation of 3-(7,8,9,10-tetrahydro-6-oxo-6H-dibenzo[b,d]pyranyl-3-oxy)-1-methylamino-2-propanol hydrochloride To a stirred solution of 7,8,9,10-tetrahydro-3-(oxiranylmethoxy)-6-oxo-6H-dibenzo[b,d]pyran (10.0 g, 0.036 m) in methanol (250 ml) and chloroform (50 ml) under an atmosphere of nitrogen was added monomethylamine (25 ml) and the mixture stirred 18 hours. The solvent was evaporated to a residue, 13.6 g, which was purified by chromatography on a Prep 500 HPLC, on silica gel, eluting with chloroform and 5% ammoniated methanol, to give a white solid. This was dissolved in absolute ethanol (200 ml) and isopropanol (200 ml), acidified with HCl gas. Upon standing, a white solid crystallized which was collected by filtration and vacuum dried to give 6.9 g of 3-(7,8,9,10-tetrahydro-6-oxo-6H-dibenzo[b,d]pyranyl-3-oxy)-1-methylamino-2-propanol hydrochloride, mp. 218°–219° C.

EXAMPLE 12

Preparation of 3-(7,8,9,10-tetrahydro-6-oxo-6H-dibenzo[b,d]pyranyl-3-oxy)-1-dimethylamino-2-propanol hydrochloride To a stirred solution of 7,8,9,10-tetrahydro-3-(oxiranylmethoxy)-6-oxo-6H-dibenzo[b,d]pyran (10.0 g, 0.036 m) in methanol (250 ml) and chloroform (50 ml) under an atmosphere of nitrogen was added dimethylamine (25 ml) and the mixture stirred 18 hours. The solvent was evaporated to an oily residue, 14.2 g. This was purified by chromatography on a Prep 500 HPLC, on silica gel, eluting with chloroform and 5% ammoniated methanol, to give a white solid. This was dissolved in isopropanol (100 ml) and methanol (100 ml) and acidified with HCl gas. Upon standing, a solid crystallized which was collected by filtration and vacuum dried to give 6.4 g of 3-(7,8,9,10-tetrahydro-6-oxo-6H-dibenzo[b,d]pyranyl-3-oxy)-1-dimethylamino-2-propanol hydrochloride, mp. 205°–206° C.

EXAMPLE 13

Preparation of 3-(7,8,9,10-tetrahydro-6-oxo-6H-dibenzo[b,d]pyranyl-3-oxy)-1-(propylamino)-2-propanol hydrochloride To a stirred solution of 7,8,9,10-tetrahydro-3-(oxiranylmethoxy)-6-oxo-6H-dibenzo[b,d]pyran (10.0 g, 0.036 m) in methanol (250 ml) and chloroform (50 ml) under an atmosphere of nitrogen was added n-propylamine (2.5 g; 0.041 m) and the mixture was stirred for 72 hours. The solvent was evaporated to an oily residue, 13.1 g, which was purified by chromatography on a Prep 500 HPLC, on silica gel, eluting with chloroform and 5% ammoniated methanol, to give 6.1 g of a white solid. This was dissolved in methanol (100 ml) and isopropanol (100 ml) and acidified with HCl gas. Upon standing, a white solid crystallized which was collected by filtration and vacuum dried to give 4.2 g of 3-(7,8,9,10-tetrahydro-6-oxo-6H-dibenzo[b,d]pyranyl-3-oxy)-1-(propylamino)-2-propanol hydrochloride, mp. 203°–204° C.

EXAMPLE 14

Preparation of 3-(7,8,9,10-tetrahydro-6-oxo-6H-dibenzo[b,d]pyranyl-3-oxy)-1-(diethylamino)-2-propanol hydrochloride To a stirred solution of 7,8,9,10-tetrahydro-3-(oxiranylmethoxy)-6-oxo-6H-dibenzo[b,d]pyran (10.0 g, 0.036 m) in methanol (250 ml) and chloroform (50 ml) under an atmosphere of nitrogen was added diethylamine (2.9 g, 0.04 m) and the mixture stirred 24 hours. The reaction was recharged with diethylamine (2.9 g, 0.04 m) and heated to 35° C. for 24 hours. The solvent was evaporated to give an oil, 13.4 g, which was purified by chromatography on a Prep 500 HPLC, on silica gel, eluting with chloroform and 5% ammoniated methanol, to give an oil, 10.6 g. This was dissolved in methanol (100 ml) and isopropanol (100 ml) and acidified with HCl gas. Upon standing, a white solid crystallized which was collected by filtration and vacuum dried to give 8.2 grams of 3-(7,8,9,10-tetrahydro-6-oxo-6H-dibenzo[b,d]pyranyl-3-oxy)-1-(diethylamino)-2-propanol hydrochloride, mp. 149°–150° C.

EXAMPLE 15

Preparation of
3-(7,8,9,10-tetrahydro-6-oxo-6H-dibenzo[b,d]pyranyl-3-oxy)-1-(1-methyl-2-phenoxyethyl)amino-2-propanol hydrochloride To a stirred solution of 7,8,9,10-tetrahydro-3-(oxiranylmethoxy)-6-oxo-6H-dibenzo[b,d]pyran (10.0 g, 0.036 m) in methanol (250 ml) and chloroform (50 ml) under an atmosphere of nitrogen was added 1-methyl-2-phenylethylamine (6.0 g, 0.04 m) and the mixture stirred for 96 hours. The solvent was evaporated to an oily residue, 14.4 g, which was purified by chromatography on a Prep 500 HPLC, on silica gel, eluting with chloroform and 5% ammoniated methanol to give 4.4 g of the pure amine base. This was dissolved in absolute ethanol (100 ml) and acidified with HCl gas. Upon standing, a white solid crystallized which was collected by filtration and vacuum dried to give 4.0 g of 3-(7,8,9,10-tetrahydro-6-oxo-6H-dibenzo[b,d]pyranyl-3-oxy)-1-(1-methyl-2-phenoxyethyl)amino-2-propanol hydrochloride, mp. 178°–179° C.

EXAMPLE 16

Preparation of
3-(7,8,9,10-tetrahydro-6-oxo-6H-dibenzo[b,d]pyranyl-3-oxy)-1-(1-pyrrolidinyl)-2-propanol hydrochloride To a stirred solution of 7,8,9,10-tetrahydro-3-(oxiranylmethoxy)-6-oxo-6H-dibenzo[b,d]pyran (10.0 g, 0.036 m) in methanol (250 ml) and chloroform (50 ml) under an atmosphere of nitrogen was added pyrrolidine (3.4 g, 0.05 m) and the mixture stirred 18 hours. The solvent was evaporated to a residue, 13.4 g, which was purified by chromatography on a Prep 500 HPLC, on silica gel, eluting with chloroform and 5% ammoniated methanol to give the pure amine base as an oil. This was dissolved in methanol (50 ml) and isopropanol (50 ml) and acidified with HCl gas. Upon standing, a white solid crystallized which was collected by filtration and vacuum dried to give 7.3 g of 3-(7,8,9,10-tetrahydro-6-oxo-6H-dibenzo[b,d]pyranyl-3-oxy)-1-(1-pyrrolidinyl)-2-propanol hydrochloride, mp. 195°–196° C.

EXAMPLE 17

Preparation of
3-(7,8,9,10-tetrahydro-6-oxo-6H-dibenzo[b,d]pyranyl-3-oxy)-1-(phenylmethyl)amino-2-propanol hydrochloride To a stirred solution of 7,8,9,10-tetrahydro-3-(oxiranylmethoxy)-6-oxo-6H-dibenzo[b,d]pyran (10.0 g, 0.036 m) in methanol (250 ml) and chloroform (50 ml) under an atmosphere of nitrogen was added benzylamine (4.3 g, 0.04 m) and the mixture stirred 48 hours. The solvent was evaporated to a residue, 13.1 g, which was purified by chromatography on a Prep 500 HPLC, on silica gel, eluting with chloroform and 5% ammoniated methanol, to give the pure free base as an oil. This was dissolved in methanol (100 ml) and isopropanol (100 ml) and acidified with HCl gas. Upon standing, a white solid crystallized which was collected by filtration and vacuum dried to give 5.7 g 3-(7,8,9,10-tetrahydro-6-oxo-6H-dibenzo[b,d]pyranyl-3-oxy)-1-(phenylmethyl)amino-2-propanol hydrochloride, mp. 222°–223° C.

EXAMPLE 18

Preparation of
3-(7,8,9,10-tetrahydro-6-oxo-6H-dibenzo[b,d]pyranyl-3-oxy)-1-(cyclopropylamino)-2-propanol hydrochloride To a stirred solution of 7,8,9,10-tetrahydro-3-(oxiranylmethoxy)-6-oxo-6H-dibenzo[b,d]pyran (10.0 g, 0.036 m) in methanol (250 ml) and chloroform (50 ml) under an atmosphere of nitrogen was added cyclopropylamine (5.7 g, 0.10 m) and the mixture stirred for 18 hours. The solvent was evaporated to an oily residue, 12.6 g, which was purified by chromatography on a Prep 500 HPLC, on silica gel, eluting with chloroform and 5% ammoniated methanol, to give the pure amine base as a solid, 6.4 g. This was dissolved methanol (150 ml) and isopropanol (150 ml) and acidified with HCl gas. Upon standing, a white solid crystallized which was collected by filtration and vacuum dried to give 5.7 g of 3-(7,8,9,10-tetrahydro-6-oxo-6H-dibenzo[b,d]pyranyl-3-oxy)-1-(cyclopropylamino)-2-propanol hydrochloride, mp. 185°–186° C.

EXAMPLE 19

Preparation of
3-(7,8,9,10-tetrahydro-6-oxo-6H-dibenzo[b,d]pyranyl-3-oxy)-1-(1,1-dimethylethyl)amino-2-propanol hydrochloride To a stirred solution of 7,8,9,10-tetrahydro-3-(oxiranylmethoxy)-6-oxo-6H-dibenzo[b,d]pyran (10.0 g, 0.036 m) in methanol (250 ml) and chloroform (50 ml) under an atmosphere of nitrogen was added t-butylamine (5.2 g, 0.072 m) and the mixture stirred for 18 hours. The solvent was evaporated to a solid residue, 13.5 g, which was purified by chromatography on a Prep 500 HPLC, on silica gel, eluting with chloroform and 5% ammoniated methanol to give the pure amine as a solid. This was dissolved in methanol (150 ml) and isopropanol (150 ml) and acidified with HCl gas. Upon standing, a white solid crystallized which was collected by filtration and vacuum dried to give 10.6 g 3-(7,8,9,10-tetrahydro-6-oxo-6H-dibenzo[b,d]pyranyl-3-oxy)-1-(1,1-dimethylethyl)amino-2-propanol hydrochloride, mp. 286°–287° C.

EXAMPLE 20

Preparation of
3-(7,8,9,10-tetrahydro-6-oxo-6H-dibenzo[b,d]pyranyl-3-oxy)-1-(2-hydroxyethyl)amino-2-propanol To a stirred solution of 7,8,9,10-tetrahydro-3-(oxiranylmethoxy)-6-oxo-6H-dibenzo[b,d]pyran (10.0 g, 0.036 m) in methanol (250 ml) and chloroform (50 ml) under an atmosphere of nitrogen was added ethanolamine (4.3 g, 0.072 m) and the mixture stirred for 48 hours. The solvent was evaporated to a residue, 13.4 g, which was purified by chromatography on a Prep 500 HPLC, on silica gel, eluting with toluene and 10% ammoniated isopropanol to give the pure amine as an oil, 8.4 g. This was dissolved in hot absolute ethanol (75 ml) and upon standing, a white solid crystallized which was collected by filtration and vacuum dried to give 5.2 g of 7,8,9,10-tetrahydro-6-oxo-6H-dibenzo[b,d]pyranyl-3-oxy)-1-(2-hydroxyethyl)amino-2-propanol, mp. 79°–80° C.

EXAMPLE 21

Preparation of
3-(7,8,9,10-tetrahydro-6-oxo-6H-dibenzo[b,d]pyranyl-3-oxy)-1-(phenylamino)-2-propanol hydrochloride To a stirred solution of 7,8,9,10-tetrahydro-3-(oxiranylmethoxy)-6-oxo-6H-dibenzo[b,d]pyran (10.0 g, 0.036 m) in methanol (250 ml) and chloroform (50 ml) under an atmosphere of nitrogen was added aniline (6.2 g, 0.074 m) and the mixture heated to reflux for 1 hour. The solvent was evaporated to a residue, 13.4 g, which was purified by chromatography on a Prep 500 HPLC, on silica gel, eluting with chloroform and 5% ammoniated methanol, to give the amine base as an oil. This was dissolved in absolute ethanol (100 ml) and ethylacetate (100 ml) and acidified with HCl gas. Upon standing, a white solid crystallized which was collected by filtration and vacuum dried to give 3.1 g of 3-(7,8,9,10-tetrahydro-6-oxo-6H-dibenzo[b,d]pyranyl-3-oxy)-1-(phenylamino)-2-propanol hydrochloride, mp. 173°–174° C.

EXAMPLE 22

Preparation of
3-(7,8,9,10-tetrahydro-6-oxo-6H-dibenzo[b,d]pyranyl-3-oxy)-1-cyclopentylamino-2-propanol hydrochloride To a stirred solution of 7,8,9,10-tetrahydro-3-(oxiranylmethoxy)-6-oxo-6H-dibenzo[b,d]pyran (10.0 g, 0.036 m) in methanol (250 ml) and chloroform (50 ml) under an atmosphere of nitrogen was added cyclopentylamine (6.3 g, 0.074 m) and the mixture heated to reflux for 1 hour. The solvent was evaporated to an oily residue, which was purified by chromatography on a Prep 500 HPLC, on silica gel, eluting with chloroform and 3% ammoniated methanol to give the pure amine base as a solid. This was dissolved in absolute ethanol (200 ml) and acidified with HCl gas. Upon standing, a white solid crystallized which was collected by filtration and vacuum dried to give 3.4 g of 3-(7,8,9,10-tetrahydro-6-oxo-6H-dibenzo[b,d]pyranyl-3-oxy)-1-cyclopentylamino-2-propanol hydrochloride, mp. 224°–225° C.

Following the procedure essentially as outlined above and substituting cycloheptylamine for cyclopentylamine will provide the corresponding 3-(7,8,9,10-tetrahydro-6-oxo-6H-dibenzo[b,d]pyranyl-3-oxy)-1-cycloheptylamino-2-propanol hydrochloride, mp. 239°–241° C.

EXAMPLE 23

Preparation of
3-(7,8,9,10-tetrahydro-6-oxo-6H-dibenzo[b,d]pyranyl-3-oxy)-1-(1H-imidazol-1-yl)-2-propanol hydrochloride To a stirred solution of 7,8,9,10-tetrahydro-3-(oxiranylmethoxy)-6-oxo-6H-dibenzo[b,d]pyran (10.0 g, 0.036 m) in methanol (250 ml) and chloroform (50 ml) under an atmosphere of nitrogen was added imidazole (2.7 g, 0.04 m) and heated to reflux for 3 hours. The solvent was evaporated to a residue, which was purified by chromatography on a Prep 500 HPLC, on silica gel, eluting with chloroform and 5% ammoniated methanol to give the pure amine base as a solid, 6.3 g. This was dissolved in absolute ethanol (100 ml) and ethylacetate (100 ml) and acidified with HCl gas. Upon standing, a white solid crystallized which was collected by filtration and vacuum dried to give 3.4 g of 3-(7,8,9,10-tetrahydro-6-oxo-6H-dibenzo[b,d]pyranyl-3-oxy)-1-(1H-imidazol-1-yl)-2-propanol hydrochloride, mp. 171°–172° C. Following the procedure essentially as outlined above and substituting pyrazole, 1,2,4-triazole or pyrrole for imidazole will result in the preparation of the corresponding 3-(7,8,9,10-tetrahydro-6-oxo-6H-dibenzo[b,d]-pyranyl-3-oxy)-1-(1-pyrazolyl)-2-propanol, 3-(7,8,9,10-tetra-hydro-6-oxo-6H-dibenzo[b,d]pyranyl-3-oxy)-1-[1-(1,2,4-triazolyl)]-2-propanol, or 3-(7,8,9,10-tetrahydro-6-oxo-6H-dibenzo[b,d]pyranyl-3-oxy)-1-(1-pyrrolyl)-2-propanol, respectively.

EXAMPLE 24

Preparation of
3-(7,8,9,10-tetrahydro-6-oxo-6H-dibenzo[b,d]pyranyl-3-oxy)-1-(6-oxo-6H-dibenzo[b,d]pyranyl-3-amino)-2-propanol To a stirred solution of 3-amino-6-oxo-6H-dibenzo[b,d]pyran (4.77 g, 0.0226 m) in methanol (1.5 L) at reflux, was added 7,8,9,10-tetrahydro-3-(oxiranylmethoxy)-6-oxo-6H-dibenzo[b,d]pyran (5.8 g, 0.021 m) and the mixture stirred for 5 days, then allowed to cool slowly to ambient temperature. A yellow solid crystallized which was collected by filtration to give 4.8 g crude product. This was dissolved in ethyleneglycol monomethylether (400 ml) at reflux, decolorized with charcoal, hot filtered and the solvent volume reduced to 200 ml. Upon standing, a yellow solid crystallized, which was collected by filtration, washed with methanol and vacuum dried to give 3.0 g of 3-(7,8,9,10-tetrahydro-6-oxo-6H-dibenzo[b,d]pyranyl-3-oxy)-1-(6-oxo-6H-dibenzo[b,d]pyranyl-3-amino)-2-propanol, mp. 209°–210° C.

EXAMPLE 25

Preparation of
3-(7,8,9,10-Tetrahydro-6-oxo-6H-dibenzo[b,d]pyranyl-3-oxy)-1-amino-2-propanol hydrochloride To a stirred solution of 7,8,9,10-tetrahydro-3-(oxiranylmethoxy)-6-oxo-6H-dibenzo[b,d]pyran (10.0 g, 0.036 ml) in methanol (250 ml) and chloroform (50 ml) under an atmosphere of nitrogen was added anhydrous ammonia (25 mls) and the mixture stirred 24 hrs. The solvent was evaporated to a residue, 13.2 g, which was purified by chromatography on a Prep 500 HPLC, on silica gel, eluting with chloroform and 10% ammoniated methanol, to give 4.2 g of an oil. This was dissolved in absolute ethanol (100 ml) and acidified with HCl gas. Upon standing, a white solid crystallized which was collected by filtration and vacuum dried to give 2.4 g of 3-(7,8,9,10-tetrahydro-6-oxo-6H-dibenzo[b,d]pyranyl-3-oxy)-1-(amino)-2-propanol hydrochloride, mp 249°–250° C.

EXAMPLE 26

Preparation of
N,N-di[3-(7,8,9,10-tetrahydro-6-oxo-6H-dibenzo[b,d]pyranyl-3-oxy)-2-hydroxypropyl]amine hydrochloride To a stirred solution of 7,8,9,10-tetrahydro-3-(oxiranylmethoxy)-6-oxo-6H-dibenzo[b,d]pyran (10.0 g, 0.036 m) in methanol (250 ml) and chloroform (50 ml) under an atmosphere of nitrogen was added anhydrous ammonia (25 ml) and the mixture stirred 24 hrs. The solvent was evaporated to a residue, 13.2 g, which was purified by chromatography on a Prep 500 HPLC, on silica gel eluting with chloroform and 10% ammoniated methanol, to give 2.3 g of an oil. This was dissolved in a mixture of methanol (25 ml), water (10 ml) and anhydrous ether (20 ml), and acidified with HCl gas. Upon standing, a white solid crystallized which was collected by filtration and vacuum dried to give 1.2 g of N,N-di[3-(7,8,9,10-tetrahydro-6-oxo-6H-dibenzo[b,d]pyranyl-3-oxy)-2-hydroxy propyl]amine hydrochloride, mp 218°-219° C.

EXAMPLE 27

Preparation of 3-(7,8,9,10-Tetrahydro-6-oxo-6H-dibenzo[b,d]pyranyl-3-oxy)-1-(4-morpholinyl)-2-propanol hydrochloride To a stirred solution of 7,8,9,10-tetrahydro-3-(oxiranylmethoxy)-6-oxo-6H-dibenzo[b,d]pyran (10.0 g, 0.036 mol) in chloroform (100 ml) and methanol (100 ml) under nitrogen was added morpholine (4.8 g, 0.55 mol) and the mixture heated to reflux for 5 hrs., cooled, and the solvent evaporated. The residue (15.4 g) was dissolved in chloroform (500 ml) and extracted with dilute HCl (500 ml). The aqueous phase was washed with chloroform (2×250 ml), basified to pH 11 with 10% NaOH and extracted with chloroform (3×250 ml). The combined extracts were dried over $MgSO_4$, and evaporated to a residue (14.5 g). This was dissolved in methanol (50 mol) and acidified with HCl gas. Upon standing a white solid crystallized which was collected by filtration and vacuum dried for 72 hrs. at 95° C. to give 8.2 g of 3-(7,8,9,10-tetrahydro-6-oxo-6H-dibenzo[b,d]pyranyl-3-oxy)-1-(4-morpholinyl)-2-propanol hydrochloride, mp. 184°-185° C.

Following the procedure essentially as outlined above and substituting thiomorpholine for morpholine will result in the preparation of the corresponding 3-(7,8,9,10-tetrahydro-6-oxo-6H-dibenzo[b,d]pyranyl-3-oxy)-1-(4-thiomorpholinyl)-2-propanol hydrochloride.

EXAMPLE 28

Preparation of 3-(7,8,9,10-Tetrahydro-6-oxo-6H-dibenzo[b,d]pyranyl-3-oxy)-1-(cycloheptylamino)-2-propanol hydrochloride To a stirred solution of 7,8,9,10-tetrahydro-3-(oxiranylmethoxy)-6-oxo-6H-dibenzo[b,d]pyran (10.0 g, 0.036 mol) in methanol (50 ml) and chloroform (200 ml) under nitrogen was added cycloheptylamine (3.0 g, 0.027 mol) and the mixture heated to reflux for 8 hrs., cooled, and the solvent evaporated to an oil, 10.4 g. This was purified by chromatography on $SiO_2$ eluting with 10% isopropanol/chloroform. Fractions were combined and evaporated to give the pure base as a white solid, 3.4 g. This was dissolved in methanol (20 ml) and isopropanol (100 ml) and acidified with HCl gas. Upon standing a white solid crystallized which was collected by filtration and vacuum dried to give 2.92 g of 3-(7,8,9,10-tetrahydro-6-oxo-6H-dibenzo[b,d]pyranyl-3-oxy)-1-(cycloheptylamino)-2-propanol-hydrochloride, mp. 239°-241° C.

EXAMPLE 29

Preparation of 3-(7,8,9,10-Tetrahydro-6-oxo-6H-dibenzo[b,d]pyranyl-3-oxy)-1-(1-piperidinyl)-2-propanol methiodide A solution of 5.0 g of 3-(7,8,9,10-tetrahydro-6-oxo-6H-dibenzo[b,d]pyranyl-3-oxy)-1-(1-piperidinyl)-2-propanol hydrochloride in water (250 ml) was basified to pH 11 and extracted with chloroform (200 ml, 2×100 ml). The organic extracts were washed with water (200 ml), dried over $MgSO_4$ and evaporated to give the white solid base. This was dissolved in hot acetone (200 ml), then treated with methyl iodide (1 ml). After standing for 6 hrs. in the dark, a white solid crystallized which was collected by filtration, washed with acetone (3×100 ml) and vacuum dried at 85° C. for 48 hrs. to give 4.8 g of 3-(7,8,9,10-tetrahydro-6-oxo-6H-dibenzo[b,d]pyranyl-3-oxy)-1-(1-piperidinyl)-2-propanol methiodide, mp. 224°-226° C. dec.

The compounds of this invention possess useful antihypoxia activity, that is, they extend the lifetime of animals exposed to a hypoxic environment. This activity is conveniently measured in mice. Groups of mice are tested at various times after the intraperitoneal administration of graded doses of the test compound. The animals' survival time in a hypoxic environment (96% nitrogen and 4% oxygen) is recorded. A statistical comparison (Wilcoxon rank sum) is made between coincident vehicle treated animals and the experimental group. The dose-response and minimum active dose (MAD) for a compound are otained. Other modes of administration can also be used.

I claim:

1. A compound having the formula:

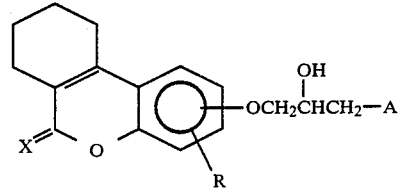

where X is oxygen or dialkyl in which each alkyl group contains one to seven carbons ($C_1$–$C_7$); R is hydrogen or alkyl containing one to seven carbons ($C_1$–$C_7$); and A is —$NR_1R_2$ where $R_1$ and $R_2$ may independently be hydrogen, $C_1$–$C_7$ alkyl, $C_3$–$C_7$ cycloalkyl, phenyl, $C_7$–$C_{10}$ phenylalkyl, $C_7$–$C_{10}$ phenoxyalkyl, $C_2$–$C_6$ alkanol, 6-oxo-6H-dibenzo[b,d]pyran-3-yl, 2-hydroxy-3-(7,8,9,10-tetrahydro-6-oxo-6H-dibenzo[b,d]pyranyl-3-oxy)propyl; or A is a heterocyclic ring of structure:

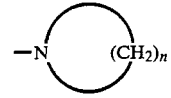

where n=2 or 3; or A is a substituted heterocyclic ring of structure:

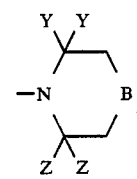

where Y and Z may be independently hydrogen or methyl and B represents a single bond, methylene, ethylene, propylene, CH-phenyl, $CHCH_2$-phenyl, oxygen, sulfur, or N—$R_4$ where $R_4$ is hydrogen, $C_1$–$C_4$ alkyl, formyl, phenyl, benzyl and where the phenyl rings may additionally be substituted with halogen, methoxy, methyl, $CF_3$, or various combinations thereof; or where A is an unsaturated heterocyclic ring taken to be 1-imidazolyl, 1-pyrrolyl, 1-pyrazolyl or 1-[1,2,4-triazolyl].

2. A compound having the formula:

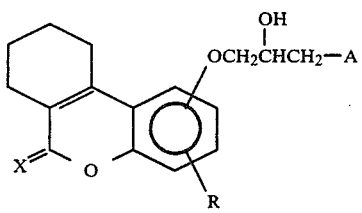

where X is oxygen or dimethyl; R is hydrogen or methyl; and A is amino, methylamino, dimethylamino, ethylamino, diethylamino, n-propylamino, isopropylamino, cyclopropylamino, t-butylamino, (2-hydroxyethyl)amino, cyclopentylamino, cycloheptylamino, 1-pyrrolidinyl, 1-piperidinyl, 4-morpholinyl, 4-thiomorpholinyl, anilino, benzylamino, 1-phenoxy-2-propylamino, 1-ethyleneiminyl, 1-trimethyleneiminyl, 1-hexamethyleneiminyl, 1-(4-phenylpiperidinyl), 1-(2,2,6,6-tetramethylpiperidinyl), 1-(4-benzylpiperidinyl), 1-piperazinyl, 1-(4-formylpiperazinyl, 1-(4-methylpiperazinyl), 1-[4-(3-chlorophenyl)piperazinyl], 1-[4-[3-(trifluoromethyl)phenyl]piperazinyl], 1-[4-(4-methoxyphenyl)piperazinyl], 1-[4-(2-methylphenyl)piperazinyl], 1-imidazolyl, 1-pyrazolyl, 1-(1,2,4-triazolyl), 1-pyrrolyl, (6-oxo-6H-dibenzo[b,d]pyran-3-yl)amino, and [2-hydroxy-3-(7,8,9,10-tetrahydro-6-oxo-6H-dibenzo[b,d]pyranyl-3-oxy)propyl]amino.

3. The compound in accordance with claim 2 where X is oxygen.

4. An acid addition salt of the compound according to claim 1.

5. A compound according to claim 1 wherein the compound is 3-(7,8,9,10-tetrahydro-6-oxo-6H-dibenzo[b,d]pyranyl-3-oxy)-1-(1-piperidinyl)-2-propanol hydrochloride.

6. A compound according to claim 1 wherein the compound is 3-(7,8,9,10-tetrahydro-6-oxo-6H-dibenzo[b,d]pyranyl-3-oxy)-1-(cyclopropylamino)-2-propanol.

7. A compound according to claim 1 wherein the compound is 3-(7,8,9,10-tetrahydro-6-oxo-6H-dibenzo[b,d]pyranyl-3-oxy)-1-(1-methylethyl)amino-2-propanol.

8. A compound according to claim 1 wherein the compound is 3-(7,8,9,10-tetrahydro-3-methyl-6-oxo-6H-dibenzo[b,d]pyranyl-1-oxy)-1-(1,1-dimethylethyl)amino-2-propanol.

9. A compound according to claim 1 wherein the compound is 3-(7,8,9,10-tetrahydro-6-oxo-6H-dibenzo[b,d]pyranyl-3-oxy)-1-(1H-imidazol-1-yl)-2-propanol hydrochloride.

10. A compound according to claim 1 wherein the compound is 3-(7,8,9,10-tetrahydro-6-oxo-6H-dibenzo[b,d]pyranyl-3-oxy)-1-(4-morpholinyl)-2-propanol hydrochloride.

11. A compound according to claim 1 wherein the compound is 3-(7,8,9,10-tetrahydro-6-oxo-6H-dibenzo[b,d]pyranyl-3-oxy)-1-(cycloheptylamino)-2-propanol hydrochloride.

12. A compound according to claim 1 wherein the compound is 3-(7,8,9,10-tetrahydro-6-oxo-6H-dibenzo[b,d]pyranyl-3-oxy)-1-(1-piperidinyl)-2-propanol methiodide.

* * * * *